US006694158B2

(12) United States Patent
Polak (10) Patent No.: US 6,694,158 B2
(45) Date of Patent: Feb. 17, 2004

(54) SYSTEM USING A PORTABLE DETECTION DEVICE FOR DETECTION OF AN ANALYTE THROUGH BODY TISSUE (75) Inventor: Anthony Polak, Lake Zurich, IL (US)

(73) Assignee: Motorola, Inc., Schaumburg, IL (US)

( * ) Notice: Subject to any disclaimer, the term of this patent is extended or adjusted under 35 U.S.C. 154(b) by 538 days.

(21) Appl. No.: 09/832,521

(22) Filed: Apr. 11, 2001

(65) Prior Publication Data
US 2002/0151772 A1 Oct. 17, 2002

(51) Int. Cl.[7] .................................................. A61B 5/00
(52) U.S. Cl. ........................ 600/310; 600/316; 600/317; 600/365
(58) Field of Search ................................. 600/310, 309, 600/316, 317, 322, 365, 347, 300; 128/903; 435/14

(56) References Cited

U.S. PATENT DOCUMENTS

| 3,877,784 A | | 4/1975 | Lin | |
|---|---|---|---|---|
| 4,058,732 A | | 11/1977 | Wieder | |
| 4,150,295 A | | 4/1979 | Wieder | |
| 4,344,438 A | | 8/1982 | Schultz | |
| 4,650,547 A | * | 3/1987 | Gough | 600/365 |
| 4,711,245 A | * | 12/1987 | Higgins et al. | 600/347 |
| 4,737,464 A | | 4/1988 | McConnell et al. | |
| 4,791,310 A | | 12/1988 | Honig et al. | |
| 4,954,435 A | | 9/1990 | Krauth | |
| 5,001,054 A | | 3/1991 | Wagner | |
| 5,061,076 A | | 10/1991 | Hurley | |
| 5,143,066 A | | 9/1992 | Komives et al. | |
| 5,156,972 A | | 10/1992 | Issachar | |
| 5,342,789 A | | 8/1994 | Chick et al. | |
| 5,496,997 A | | 3/1996 | Pope | |

(List continued on next page.)

FOREIGN PATENT DOCUMENTS

| EP | 0761159 A3 B1 | 3/1998 |
|---|---|---|
| WO | WO 00/20862 | 4/2000 |

OTHER PUBLICATIONS

Sohrab Mansouri and Jerome S. Schultz, "A Miniature Optical Glucose Sensor Based On Affinity Binding", Biotechnology, 1984, pp 885–890.

W. Rudolf Seitz, "Optical Sensors Based In Immobilized Reagents", Biosensors Fundamentals and Applications, Oxford University Press, copyright 1987, pp 599–603.

D. L. Meadows and J. S. Schultz, "Design, Manufacture and Characterization of an Optical Fiber Glucose Affinity Sensor Based on An Homogeneous Fluorescence Energy Transfer Assay System", Analytica Chimica Acta 280, 1993, pp 21–30.

Klaus Mosbach and Olof Ramström, "The Emerging Technique of Molecular Imprinting and Its Future on Biotechnology", Bio/Technogoly vol. 14, 1996, pp 163–170.

Margaret A. Hines et al., Synthesis and Characterization of Strongly Liminescing ZnS–Capped CdSe Nanocrystals, J. Phys. Chem., 100, 1996, pp 468–471.

Dmitri Ivnitski et al., "Biosensors for Detection of Pathogenic Bacteria", Biosensors and Bioelectrics 14, 1999, pp 599–624.

(List continued on next page.)

Primary Examiner—Henry Bennett
Assistant Examiner—Fadi H. Dahbour (57) ABSTRACT

A portable optical system includes interrogation of an implanted sensor located in a body tissue. The sensor contains a labeled analogue and a reference, which emit light at different wavelengths. The external optical instrument detects and discriminates between light from the labeled analogue and light from the reference. Logic in the detector receives and processes signals from the detector and generates an indication of the detected analyte level.

56 Claims, 5 Drawing Sheets

U.S. PATENT DOCUMENTS

| | | | |
|---|---|---|---|
| 5,605,152 A | 2/1997 | Slate et al. | |
| 5,660,848 A | 8/1997 | Moo-Young | |
| 5,756,115 A | 5/1998 | Moo-Young | |
| 5,814,449 A | 9/1998 | Schultz et al. | |
| 5,871,628 A | 2/1999 | Dabiri et al. | |
| 5,990,479 A | 11/1999 | Weiss | |
| 5,995,860 A | 11/1999 | Sun et al. | |
| 6,002,954 A | 12/1999 | Van Antwerp et al. | |
| 6,011,984 A | 1/2000 | Van Antwerp et al. | |
| 6,040,194 A | 3/2000 | Chick et al. | |
| 6,049,727 A | 4/2000 | Crothall | |
| 6,081,736 A | 6/2000 | Colvin et al. | |
| 6,110,630 A | 8/2000 | Reddy et al. | |
| 6,114,038 A | 9/2000 | Castro et al. | |
| 6,114,350 A | 9/2000 | Randall et al. | |
| 6,121,075 A | 9/2000 | Yamashita | |
| 6,134,461 A | 10/2000 | Say et al. | |
| 6,163,714 A | 12/2000 | Stanley et al. | |
| 6,177,684 B1 | 1/2001 | Sugiyama | |
| 6,216,022 B1 * | 4/2001 | Tyrrell et al. | 600/310 |
| 6,251,303 B1 | 6/2001 | Bawendi et al. | |
| 6,256,522 B1 | 7/2001 | Schultz | |
| 6,274,323 B1 | 8/2001 | Bruchez et al. | |
| 6,379,622 B1 | 4/2002 | Polak et al. | |
| 6,383,767 B1 * | 5/2002 | Polak | 435/14 |
| 6,432,050 B1 * | 8/2002 | Porat et al. | 600/300 |
| 6,438,397 B1 * | 8/2002 | Bosquet et al. | 600/310 |
| 6,441,747 B1 * | 8/2002 | Khair et al. | 128/903 |
| 6,454,710 B1 | 9/2002 | Ballerstadt et al. | |

OTHER PUBLICATIONS

Ryan J. Russell et al., "A Fluorescense–Based Glucose Biosensor Using Concanavalin A and Dextran Encapsulated In A Poly(ethylene glycol) Hydrogel", Analytical Chemistry Vo. 71, No. 15, 1999, pp. 3126–3132.

M. Dittrich et al., "Branched Oligoester Microspheres Fabricated By A Rapid Emulsion Solvent Extraction Method", J. Microencapsulation, vol. 17, No. 5, 2000, pp 587–598.

J. Molpeceres et al., "Biodegradable Nanoparticles As A Delivery System For Cyclosporine: Preparation and Characterization", J. Microencapsulation, vol. 17, No. 5, 2000, pp 599–614.

Ralph Ballerstadt and Jerome S. Schultz, "A Fluorescence Affinity Hollow Fiber Sensor For Continuous Transdermal Glucose Monitoring", Analytical Chemistry vol. 72 No. 17, 2000, pp 4185–4192.

The Nut Factory: Kitchen: Interesting Facts: Chocolate Panning:, "Panning Nuts in Chocolate", <http://www.thenutfactory.com/kitchen/facts/facts–chocolate–panning-.html>, Mar. 16, 2001, pp 1–4.

John Franjione, Ph. D. et al.—Technology Today—Art & Science Microencapsulation, "The Art and Science of Microencapsulation", <http://www.swri.org/3pubs/ttoday/summer/microeng.htm>, Mar. 16, 2002, pp 1–7.

* cited by examiner

SYSTEM USING A PORTABLE DETECTION DEVICE FOR DETECTION OF AN ANALYTE THROUGH BODY TISSUE

BACKGROUND

The present invention relates to a system and method for qualitatively/quantitative detection of an analyte in a sample and more particularly, a system using an implantable sensor beneath the skin and a portable detection device that can take measurements non-invasively.

Various devices and methods have been provided for monitoring concentrations or levels of analytes in humans and other animals to determine certain conditions of a subject, including analysis of diseases present. Present devices and methods used to monitor many conditions, however, are intrusive and may have undesirable or deleterious effects. For example, persons with diabetes may need to continuously monitor their glucose levels. Typically, a patient draws and analyzes glucose levels in his/her own blood multiple (6–8) times daily to accurately control their glucose level. A substantial proportion of diabetics do not perform this task because with available techniques it may be awkward, time consuming, and sometimes painful.

Rather than drawing blood with a needle and measuring the glucose levels externally, other methods have focused on in situ analysis of the glucose levels in subcutaneous fluid, which correlates with the concentration of the glucose in the bloodstream. One of the methods to measure the glucose levels requires puncturing the dermal tissue and inserting an optical fiber, which has a structure on the end embedded in the subcutaneous fluid. The structure houses chemicals that fluorescence when activated by glucose molecules and may have a mirror on the end of the structure opposing the end of the optical fiber. The end of the fiber is attached to a photomultiplier tube, which detects the amount of fluorescence. However, this type of system is inefficient, large and bulky, and the optical fiber through the skin may pose risk.

In an attempt to avoid the problems associated with an optical fiber puncturing and held through the skin, implantable optical analyte-sensors have recently been developed. These sensors are implanted under the dermal tissue and placed in the subcutaneous fluid during an operation. The sensors are optically interrogated, thereby preventing the need to penetrate the skin to determine glucose levels.

However, optically interrogated sensors have proven unworkable over extended use time periods due in part to mechanical reasons, such as leakage at the assembly seams, and chemical reasons, such as photobleaching of the fluorescent labels present inside the sensor, which require frequent calibration.

However, numerous other problems exist for systems using the conventional implanted sensors. For example, in general the excitation-source and detector remain full sized (such as a packaged laser and photomultiplier tube) and thus remote to the sensor. Furthermore, because both the excitation-source and detector are remote to the sensor, optical fibers are used, in this case to transmit the excitation light from the excitation-source to the sensor and response light from the sensor to the detector. This system is thus both cumbersome and expensive.

BRIEF SUMMARY

In view of the above, a portable device that monitors analyte levels and provides an indication of the level, is relatively small, and can be used to take readings in a non-invasive manner is provided by using a combination of a portable instrument with a novel configuration and a novel reference source. The system also provides compensation for photodrift and other conventional problems thereby extending the interval between any necessary calibration. Similarly, a method for monitoring analyte levels and providing an indication of the level is provided.

In one embodiment, the optical irradiation system includes a sensor disposed beneath a user's dermal tissue that contains a fluorescently labeled analogue, and a reference. The labeled analogue and reference are in close proximity with each other. The labeled analogue emits a first electromagnetic signal and the reference emits a second electromagnetic signal having a different wavelength than the first electromagnetic signal. The fluorescent intensity of the labeled analogue is proportional to the concentration of the analyte of interest. By measuring the intensity of the labeled analogue, the concentration of analyte may be calculated. The optical irradiation system also includes a portable instrument that is used external to the dermal tissue. When a reading is taken, the portable instrument is placed above and adjacent to the sensor.

The portable instrument includes an optical excitation-source, for example a laser diode, which generates radiation and irradiates the sensor through the dermal tissue. A receiver in the portable instrument detects and discriminates between the two electromagnetic signals and produces a first electrical signal corresponding to the first electromagnetic signal and a second electrical signal corresponding to the second electromagnetic signal. Logic in the portable instrument receives and processes the first and second electrical signals and generates an indication of the detected analyte level.

The portable instrument can be placed on or adjacent to the user's skin. One benefit of placing a reference in close proximity to the labeled analogue is the ability to maximize the emission intensity available from the labeled analogue emitter by maximizing the emission intensity from the reference. When the analyte sensing device is implanted, and the excitation-source or laser is above the skin, the invariant (analyte independent) nature of the reference emission may be used to fine tune the position of the external device in relation to the implant for maximum signal.

In another aspect of the invention, the configuration of an optical element in the portable instrument is such that the optical element increases the light gathering ability of the device, and directs the radiation from the sensor to substantially impinge on the receiver at an angle less than about 20° from normal, so that full advantage can be taken of the interference filters used to discriminate between the two electromagnetic signals.

The following figures and detailed description of the preferred embodiments will more clearly demonstrate these and other advantages of the invention.

DETAILED DESCRIPTION

Figure 1:
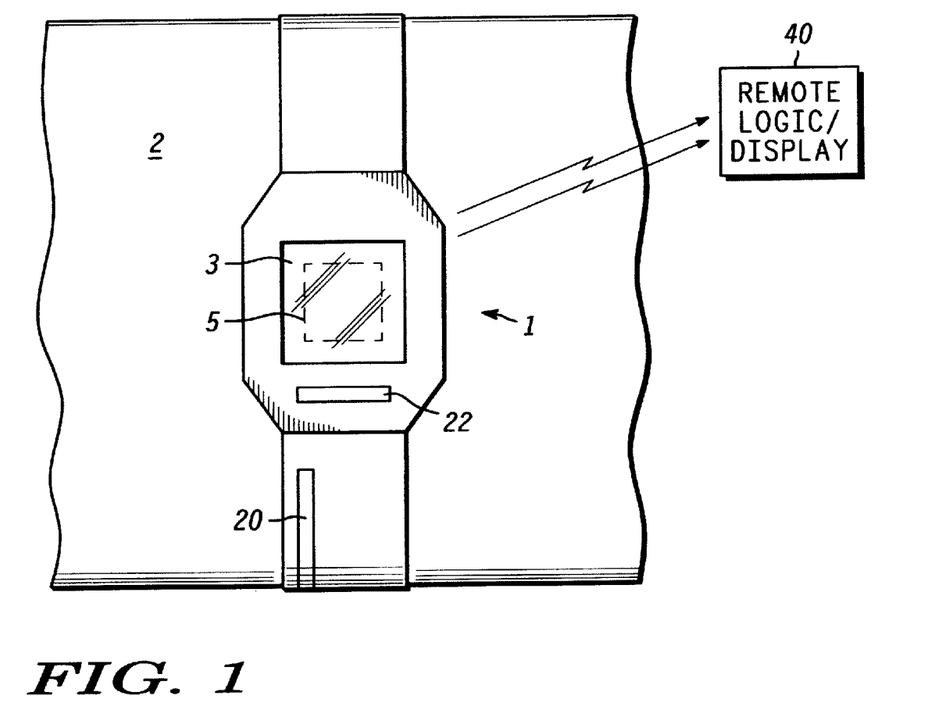
FIG. 1 illustrates a top view of an embodiment of the portable instrument of the present invention.
Figure 2:
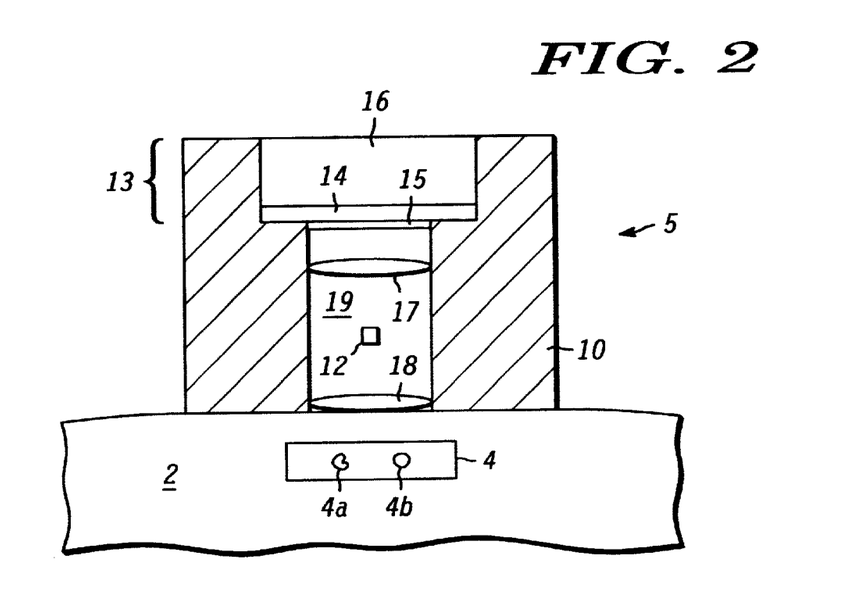
FIG. 2 illustrates a partial sectional view of an embodiment of the portable instrument of the present invention.
Figure 4:
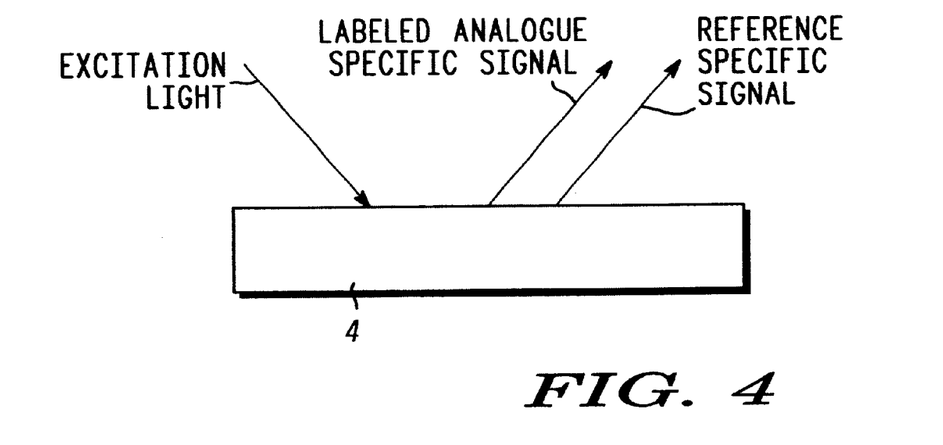
FIG. 4 illustrates operation of an embodiment of the sensor of the present invention.

FIGS. 1 and 2 illustrate one embodiment of the system of the present invention, which includes a small, portable instrument 1 and an analyte sensing device (sensor) 4. In this embodiment, a detection device 5 is contained in the portable instrument 1, which preferably has a display 3. The portable instrument 1 and detection device 5 contained within the instrument 1 are disposed above the dermal tissue 2 and above and adjacent to a sensor 4 implanted below dermal tissue 2. The sensor 4 contains the fluorescently labeled analogue 4a and a reference 4b, which emit or radiate electromagnetic energy of a specific wavelength when absorbing electromagnetic energy of a smaller wavelength. The labeled analogue 4a thus fluoresces at a different wavelength from the luminescence of the reference 4b, thereby allowing subsequent individual detection, as described in more detail below. The sensor 4 emits radiation in a 360° field (if a reflective backplane (not shown) is added to the sensor 4, the sensor 4 will effectively emit radiation in a 180° field). One example of the manner in which the sensor 4 operates is shown in FIG. 4.

To accurately analyze the concentration of labeled analogue 4a, the labeled analogue 4a and reference 4b are disposed physically close enough together such that the electromagnetic energy from both is detectable at the same time. The detection device 5 is disposed above the dermal tissue 2 and adjacent to the sensor 4 such that sufficient radiation from the sensor 4 may be detected by the detection device 5 to determine the concentration of the labeled analogue 4a. Preferably, the wavelengths of the electromagnetic signals from the labeled analogue 4a and the reference 4b do not substantially overlap so that the signals from each of these sources may be detected individually, as described below. Preferred embodiments of the sensor are described in U.S. patent application Ser. No. 09/832,575, entitled "DEVICES AND METHODS FOR MONITORING AN ANALYTE", and U.S. patent application Ser. No. 09/832,663, entitled "SENSOR DEVICE AND METHODS FOR MANUFACTURE" filed concurrently herewith, the content of both which is incorporated herein by reference in their entirety.

A well-known problem associated with fluorescent dyes and optical measurements is that the fluorescent response (intensity) of an optical sensor is dependent on the intensity of the light that irradiates it. The intensity of the light that strikes the optical sensor is in turn dependent upon the optical path length and the absorptivity and scattering of the media that the light must travel through before it reaches the monitoring device, and the path the fluorescent signal must take in order to reach the detector. In addition, any variation in the intensity of the power output of the light emitting device will be interpreted as a change in the concentration of the labeled analogue, and hence a change in the concentration of the analyte.

Various approaches have been used to solve this problem. One strategy is to incorporate a separate internal reference dye in the sensor.

The reference dye can be an organic dye, which fluoresces (emits) at a substantially different wavelength than the dye or label attached to the analogue. The excitation wavelength of the reference dye can be the same as the dye attached to the analogue or different.

By physically moving the light source and photodetector the intensity of the reference, dye can be monitored and optimized. Since the reference dye is part of the implanted package, light from the reference and labeled analogue dye travel substantially the same path to the detector, resulting in a similar attenuation due to scattering, absorption and path length. Therefore, by ratioing the intensity of the labeled analogue to reference intensity any effects due to scattering, absorptivity (skin color) or path length is removed.

The reference can be an organic dye, such as TRACER DYE (Molecular Probes, Eugene, Oreg.), or quantum dots. Quantum dots are particles that measure only a few nanometers in diameter that make =particularly good reference sources. They come in a nearly unlimited palette of colors and can be linked to other molecules (such as bio-molecules, including proteins and polynucleotides, glass, and plastic) to adjust their solubility. The emission wavelength of quantum dots can be varied by varying the size of the nanoparticles and can be used to make a variety of colors (emission wavelengths) with white light or a single-color excitation-source. Furthermore, the quantum dots display a greater photostability than traditional organic dyes. A more detailed description of the quantum dot is described in U.S. patent application Ser. No. 09/832,538, entitled "SENSOR INCORPORATING A QUANTUM DOT AS A REFERENCE", filed concurrently herewith, the content of which is incorporated herein by reference in its entirety.

The detection device 5 is disposed above the dermal tissue and includes an excitation-source 12, a receiver 13, and lenses 15, 17, 18. The excitation-source 12, receiver 13, and lenses 15, 17, 18 are housed in a medium 10. The detection device 5 may be incorporated with logic 22 in the portable instrument 1. The portable instrument 1 may preferably have a configuration similar to that of a wristwatch.

The excitation-source 12 emits electromagnetic radiation of a wavelength that penetrates the dermal tissue 2 and is absorbed minimally before impinging upon the sensor 4. The electromagnetic radiation from the excitation-source 12 that reaches the sensor 4 is substantially absorbed by the labeled analogue 4a and reference 4b. Preferably, this electromagnetic radiation is in the optical region of the spectrum. The optical region of the spectrum may be defined here as visible or near infrared light (light of about wavelengths about 400 nm up to about 2 μm). Preferable ranges of wavelength of the excitation-source 12 include, from about 630 nm to about 1.2 μm or about 630 nm to about 800 nm.

The excitation-source 12 preferably may be a laser diode, which emits a high intensity beam in a relatively small area. The laser diode may irradiate the sensor 4 without requiring any focusing optics. The free-space radiation pattern of the laser diode is generally a non-$TEM_{00}$ mode with a 10°/40° distribution, depending on the optical axis. The natural radiation pattern of the diode may be used to excite substantially the entirety of the sensor 4 without the use of external optical elements (such as lenses or optical fibers) to guide the optical radiation. The excitation-source 12 may be operated in a pulsed mode. When activated in this pulsed mode, the excitation-source 12 may irradiate the sensor 4 with a single pulse of about 1 μs to about 1 second duration, preferably about 100 μs to about 10 ms, or multiple pulses of similar duration. In the latter case, the multiple pulses may be separated by less than 1 second, preferably less than about 10 ms. Pulsed operation of the excitation-source 12 conserves energy of the power source 20 connected with the excitation-source 12. Continuous operation of the excitation-source 12, however, may be desired, in which case the concentration of labeled analogue 4a (and hence analyte) may be continuously monitored at the expense of power consumed.

Other excitation-sources well known in the art, such as light emitting diodes, may also be used. However, using other excitation-sources may decrease the intensity of radiation reaching the labeled analogue 4a and reference 4b (by both decreasing the overall intensity and increasing the area of radiation), thereby causing a lower emission from both and requiring focusing optics.

Emissions from the labeled analogue 4a and reference 4b impinge on the receiver 13. The receiver 13 may respond to a wide range of wavelengths, including those from both the labeled analogue 4a (which may fluoresce at wavelengths of greater than about 630 nm, preferably about 647 nm) and reference 4b (which may emit at wavelengths of greater than about 670 nm, preferably about 760 nm). The receiver 13 may include combinations of detectors 16 and filters 14. The detectors 16 detect electromagnetic energy and generate electrical current in response to the detected energy. The detectors 16 may be any broad band, small size detectors well known in the art, but are preferably photodiodes.

Figure 3:
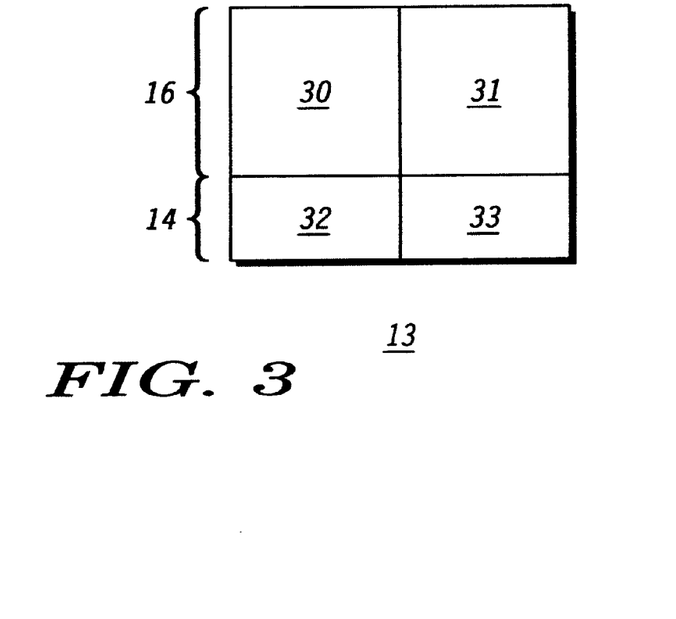
FIG. 3 illustrates a partial sectional view of an embodiment of a receiver of the portable instrument of the present invention.

One example of the receiver 13 of the first embodiment is shown in FIG. 3, in which the receiver 13 preferably includes at least two photodiodes 30, 31 and at least two corresponding filters 32, 33. In this embodiment, the excitation-source 12 is disposed between the sensor 4 and the receiver 13. However, since the excitation-source 12 may be much smaller than the receiver 13, the placement of the excitation-source 12 may have little impact on the total intensity of emissions from the sensor 4 that impinge on the receiver 13.

The filters 14 filter emissions from the excitation-source 12. The filters 14 may additionally filter emissions from either the labeled analogue 4a or the reference 4b. As the excitation-source 12 emits light of a shorter wavelength than either the labeled analogue 4a or reference 4b, several types of filters well known in the art may be used to pass emissions from the labeled analogue 4a and/or reference 4b: long-pass filters, colored filters, interference filters, or band-pass filters. The filters 14 are preferably disposed between the detectors 16 and the excitation-source 12, and thus between the detectors 16 and the sensor 4. The filters 14 increase the signal/noise ratio of the overall detection device 5.

In addition, a Fresnel lens 15 may be disposed between the filters 14 and the sensor 4, to form a collimated beam of light, which then strikes the interference filter 14 with near normal incidence. The optical properties of an interference filter are optimized for normal incidence. The addition of a Fresnel lens insures that only light of the appropriate wavelength passes through the filter (by controlling the angle of incidence) to the detector 16. In this case, backscattered light from the excitation-source 12 is blocked and only emission from the labeled analogue 4a or reference 4b enters the detector 16. Although as shown in FIG. 2, the Fresnel lens 15 is preferably disposed between the filters 14 and the excitation-source 12, it may be located anywhere between the receiver 13 and the end of the aperture 19 (described in more detail below). The Fresnel lens 15 may also be used in place of one or both of the other lenses 17, 18. The Fresnel lens 15 may preferably be composed of a thin plastic and thus lighter than conventional glass lenses.

In the embodiment shown in FIG. 2, the detectors 16 are preferably independent detectors and the filters 14 are preferably independent filters. Thus, one filter may reject light from the labeled analogue 4a (while transmitting light from the reference 4b) while the other filter rejects light from the reference 4b (while transmitting light from the labeled analogue 4a). In this case, the excitation-source 12 may pulse once and the independent detectors read at substantially the same time to independently determine the signal from the labeled analogue 4a and the signal from the reference 4b.

The lenses 17, 18, receive emissions from the sensor 4, collimate the emissions, and subsequently focus the collimated emissions onto the filters 14. In addition the lenses 17, 18 increase the numeric aperture of the system, giving the system more light gathering capability and increasing the signal to noise ratio. The lenses 17, 18 are disposed between the filters 14 and the sensor 4. The surfaces of the lenses 17, 18 may be coated with appropriate anti-reflection coatings (not shown) depending on whether the particular surface is an interface between the lens and air (index of refraction of about 1) or between the lens and the dermal tissue 2 (index of refraction of about 1.4–1.45). Preferably, the lenses 17, 18 may be composed of PMMA and the coatings may be produced by North American Optics and composed of thin alternating layers of $TiO_2$ or $Al_2O_3$ and $SiO_2$. One of the lenses 17 may additionally focus the excitation radiation from the excitation-source onto the sensor 4, thereby allowing a smaller sensor 4 to be implanted.

As the lenses 17, 18 are disposed closer to the source of emissions of the sensor 4 than the receiver 13, the lenses 17, 18 increase the amount of emission from the sensor 4 received by the receiver 13. In addition, the lenses 17, 18 may decrease the incident angle of received emissions to be less than about 20° from normal. This may be important for filters that require an incident angle of less than about 200 from normal to adequately act as a filter. The focusing lens 18 may be disposed between the excitation-source 12 and the sensor 4, while the collimating lens 17 may be disposed between the excitation-source 12 and the filters 14.

An aperture 19 is fabricated in the medium 10 of FIG. 2. Medium 10 may be formed of any material that is moldable or machineable and optically opaque, such as a filled plastic (e.g. polyphenylene sulfide, Nylon, polyethylene with carbon black filler). The aperture 19 may be up to about the size of the sensor 4, preferably between about ¼ and about ¾ the size of the sensor 4. The excitation-source 12, receiver 13, and lenses 15, 17, 18 are subsequently positioned and fixed in the aperture 19. These elements may be embedded in the aperture 19 by later processing.

The aperture 19 does not necessarily require a constant diameter throughout the detection device 5. As shown in FIG. 2, for example, the aperture 19 is larger where receiver 13 (both detectors 16 and filters 14) is located than where the lenses 17, 18 and excitation-source 12 are located. The surfaces of the medium 10 opposing the sensor 4, including the aperture 19, may be planar, i.e. the excitation-source 12, receiver 13, and lenses 17, 18 may be disposed within the aperture 19 such that none of the elements extend outside of the plane of the surface of the medium 10. This may allow the detection device 5 to be more secure as none of the elements are exposed. The aperture 19 may also collimate emissions from the sensor 4 such that the emissions from the sensor 4 substantially impinge on the filter 14 at an angle of less than about 20°. The elements disposed in the aperture 19 (e.g. excitation-source 12, receiver 13, lenses 17, 18) may be fixed by a variety of methods, preferably being held by set screws (not shown). As defined herein, an optical element may comprise the lenses 15, 17, 18 or the aperture 19.

The optical emissions detected by the receiver 13 are transformed into electrical signals and subsequently transmitted to and processed by logic 22. Logic, as referred to here, encompasses both digital and analog electronics. For example, the logic 22 may include an analog-to-digital (A/D) converter that transmits digital signals to a microprocessor that is programmed to perform the appropriate calculations to convert the signals to a concentration. Alternatively, dedicated analog circuits may be used to perform the same function.

The logic 22 may determine the concentration of labeled analogue 4a in the sensor 4, convert this to an analyte concentration and then store or display this information on a local display 3. The local logic 22 may also process the signals and transmit data to remote logic 40, via a transmitter (not shown), which then further process and/or display the concentration of the analyte.

In a preferred embodiment, the logic 22, 40 may receive information from the detectors 16 in the form of individual currents, convert the currents to corresponding voltages using transimpedance amplifiers (not shown) or other techniques well known in the art, and then convert the voltages to corresponding digital signals using an analog-to-digital (A/D) converter (not shown) before or after transmission. The A/D converters may gate through voltages from the current-to-voltage converters at a predetermined time after the excitation-source 12 has been activated. The logic 22 may include a microprocessor (not shown) to control the electronics, manipulate the digital signals, and/or determine the concentration as above.

The concentration of labeled analogue 4a (and hence analyte) present in the sensor 4 may be determined by normalizing the strength of the electromagnetic signal from the labeled analogue 4a with that from the reference 4b from a single pulse or multiple pulses of the excitation-source 12.

Other methods of determining the concentration of labeled analogue 4a include observing the time response of the electromagnetic signal or the rate of change of the labeled analogue 4a concentration over several measurements rather than the overall concentration of labeled analogue 4a at a single measurement. One advantage of normalization allows the local logic 22 or remote logic 40 to compensate for a change in signal strength from the labeled analogue 4a caused by external sources, e.g. misalignment of the instrument 1 over the sensor 4, change in intensity from the excitation-source 12, change in absorption by the dermal tissue 2, or photodecomposition. The resultant labeled analogue 4a signal strength may then be compared with values stored in a look-table stored in a memory element in the instrument 1 to determine and display the analyte concentration. The labeled analogue 4a concentration may be determined singularly at the time the detection device 5 is activated or continuously after activation.

Alternatively, the logic 22 may determine whether the labeled analogue 4a (and hence analyte) in the sensor 4 is outside of a preset limitation, i.e. has exceeded a reference concentration or decreased below the reference concentration rather than specifically determining the concentration. In this case, the signals, in the form of current, may be transformed into voltage using the methods described above and subsequently compared to a reference voltage corresponding to the set concentration. The logic 22 may also include an indicator, such as an audible alarm or LED or screen display that indicates when the determined voltage is outside of the preset limitation. In one preferred embodiment, the pager electronics in a Timex pager watch may be replaced by the detection device 5 and logic 22.

Figure 5A:
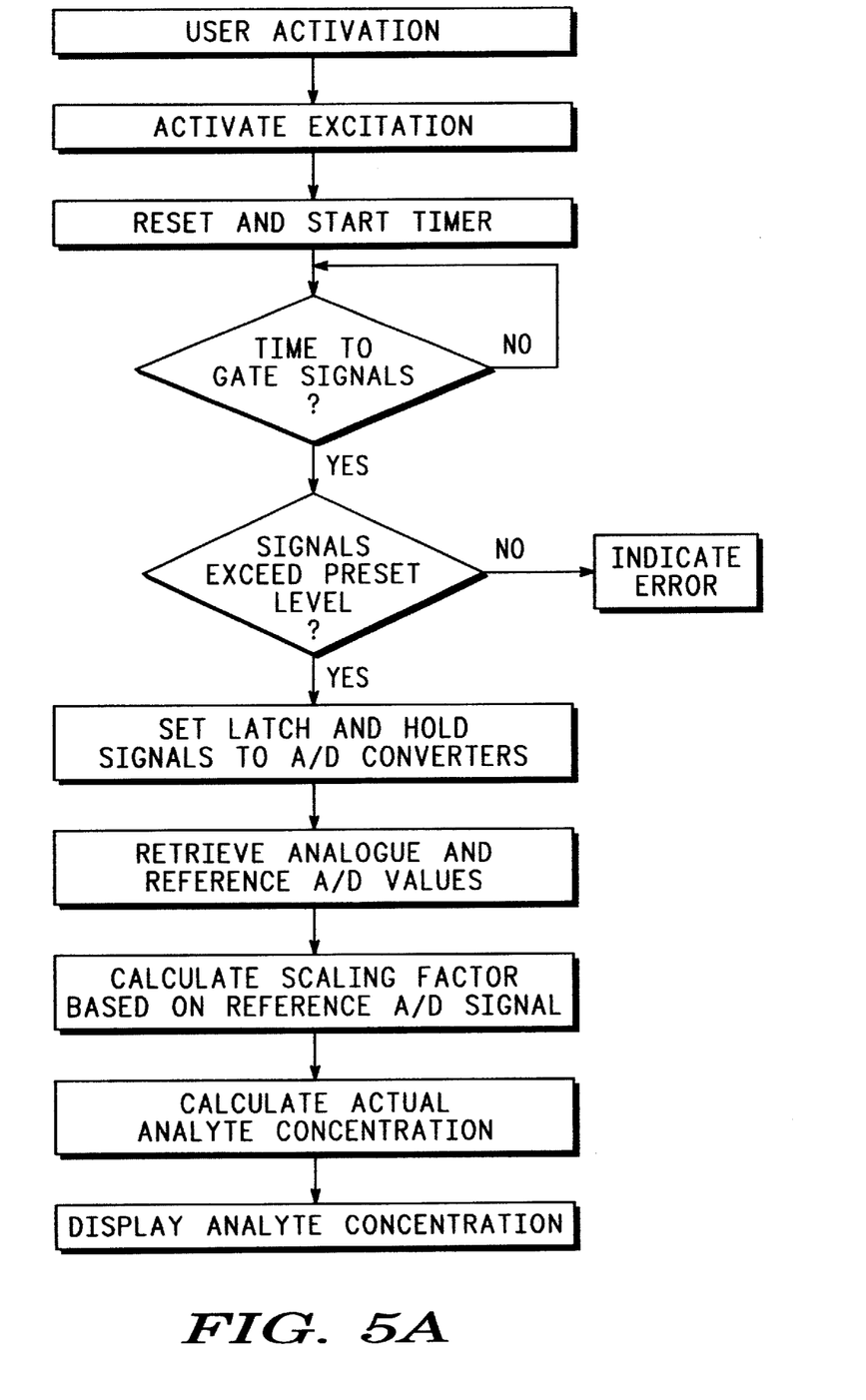
FIG. 5a illustrates a flowchart of a first embodiment of a program in the microprocessor of the present invention.

FIG. 5a illustrates a flowchart of a preferred program in the microprocessor of the logic 22. The user activates the analyte monitor function on the instrument 1. A signal is sent to the microprocessor, which then activates the excitation-source 12 and starts a timer. The microprocessor waits for a predetermined amount of time and gates in the voltages corresponding to the labeled analogue 4a and reference 4b signals from the A/D converters. If signals are not received or either signal (and thus corresponding digital signal) is below a set level, the microprocessor displays an error message on the display 3. If the signals exceed the set level, then the microprocessor processes the output of the A/D converters. During processing, the microprocessor normalizes the input corresponding to the labeled analogue 4a signal using the input corresponding to the reference signal 4b. The microprocessor then may calculate the concentration of the analyte and subsequently generates an indication of the result by displaying the result on the display 3.

Figure 5B:
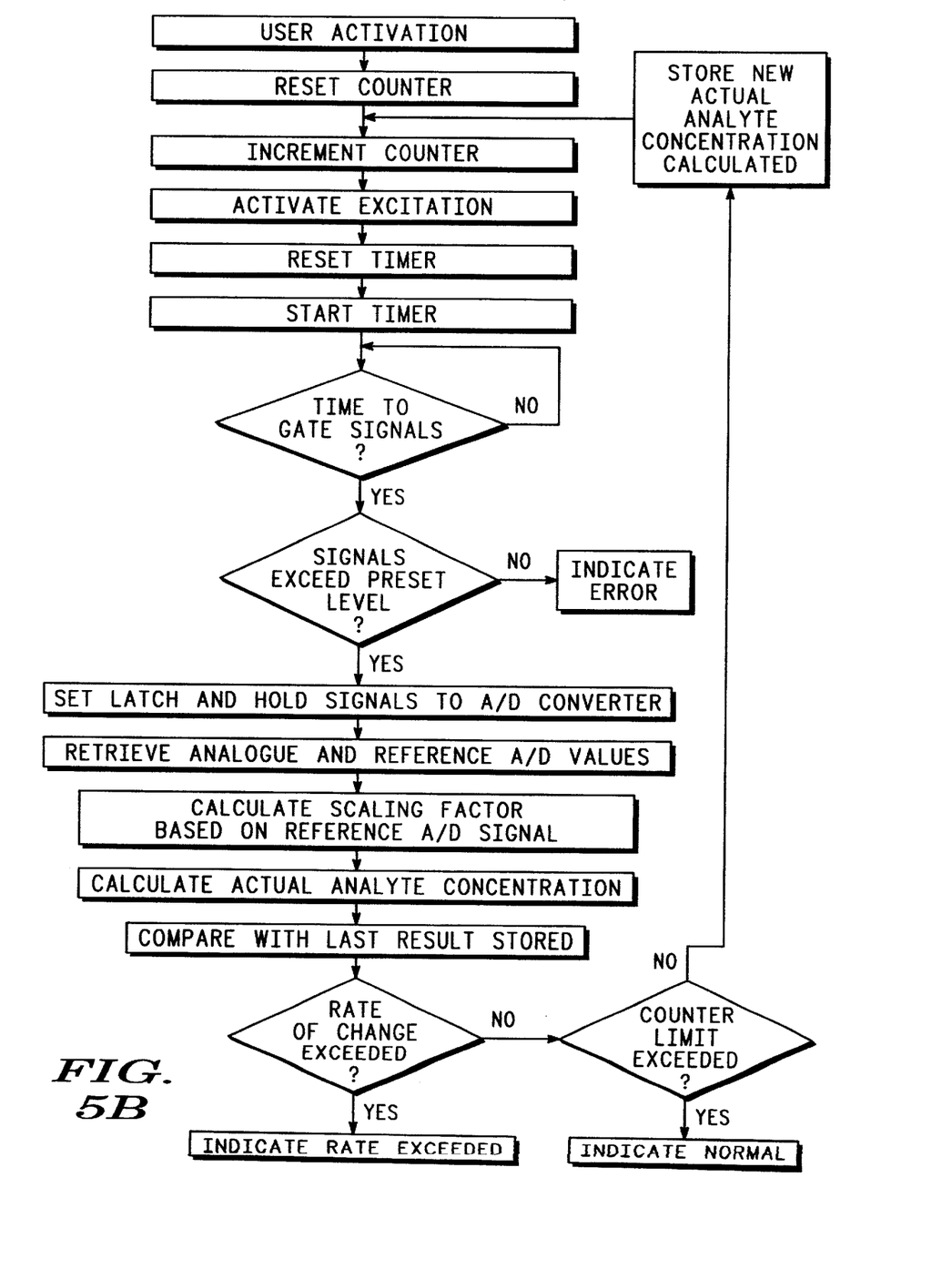
FIG. 5b illustrates a flowchart of a second embodiment of a program in the microprocessor of the present invention.

Alternatively, the microprocessor may compare normalized result to a preset result and activate the indicator (e.g. alarm) on the instrument 1 if the normalized result is larger/smaller than the preset result. In addition, the microprocessor may store the normalized result/concentration in the memory element and then be used to later recall the result and/or time of the result using other functions on the instrument 1. Similarly, the microprocessor may successively trigger the excitation-source 12 a set number of times, determine the normalized result/concentration after each excitation, store the information, determined rate of change of the analyte, and indicate whether the rate of change exceeds a predetermined amount, as shown in FIG. 5b.

The signal and power lines (not shown) to the electronic components (e.g. detectors 16, excitation-source 12, and possibly filters 14) may be formed of an optically transparent conductor, such as indium tin oxide (ITO). Although an external battery 20 is shown in FIG. 1, an internal battery (not shown) may be included in the instrument 1 to provide voltage/power to the detectors 16, excitation-source 12, and possibly filters 14.

Presently, a Timex Ironman Triathlon, Internet/Messenger watch, was used as the portable instrument. The electronics necessary for the pager function was removed from the Timex watch and replaced with the logic and the medium housing the excitation-source and receiver. The functional switches on the Timex watch that used to activate the pager functions were then used to activate the sensing system instead.

Alternate embodiments of the detection device 5 include using only a single lens to either focus or collimate the light from the sensor 4 rather than using multiple lenses, thereby decreasing loss due to the second lens. The lens preferably may be disposed between the excitation-source 12 and the sensor 4 to intersect the maximum area of emission from the sensor 4.

In another embodiment (not shown), a single detector/filter combination may be used. In this embodiment, either the detector or the filter may be electrically tunable to reject one or more of the wavelengths corresponding to the labeled analogue 4a and the reference 4b. For example, the excitation-source 12 may pulse once while one of the detector or filter rejects one of the wavelengths and then pulse a second time while the same device rejects the other wavelength (or the other device rejects the other wavelength).

Alternatively, the filters 14 may be eliminated and two independent detectors 16 form the receiver 13. In this case, however, the detectors 16 discriminate between signals from the labeled analogue 4a and signals from the reference 4b. Here, one detector may be a non-tunable detector that does not respond to light having the wavelength of the labeled analogue 4a, while the other detector may be a non-tunable detector that does not respond to light having the wavelength of the reference 4b. Detectors of this type are well known in the art, for example, semiconductor quantum well detectors. A single pulse from the excitation-source 12 may be used and electromagnetic emission independently detected from the labeled analogue 4a and the reference 4b.

Another embodiment, combining the above, may use a single tunable detector, without any filters, that responds to light from only one of the labeled analogue 4a or the reference 4b when tuned to a first voltage and responds to light of the other of the labeled analogue 4a or the reference 4b when tuned to a second voltage. In this case, two pulses from the excitation-source 12 are required to discriminate between the emitted signals, one with the detector tuned at the first voltage and another with the detector tuned to the second voltage.

In another embodiment, rather than use independent detectors and/or filters, two different excitation-sources may be provided, one having a wavelength sufficient to excite both the labeled analogue 4a and the reference 4b, and the other having a wavelength sufficient to excite only the labeled analogue 4a or the reference 4b. For example, if the labeled analogue 4a fluoresces at about 647 nm and reference 4b emits about 760 nm, and the labeled analogue 4a absorbs at below about 647 nm and the reference 4b absorbs below about 700 nm, one excitation-source may be chosen to emit below about 647 nm and the other excitation-source to emit between about 647 nm and about 700 nm (in a region where there is minimal overlap with the absorption spectrum of the labeled analogue 4a). In this case, two (or more) measurements may be taken with one or the other excitation-source emitting. The resultant signal from the reference 4b, when the excitation-source between about 647 nm and about 700 nm is operated, is then processed with the resultant signal from both the labeled analogue 4a and the reference 4b, when the excitation-source below about 647 nm is operated, to determine the concentration of the labeled analogue 4a, and hence the concentration of the analyte.

Figure 6:
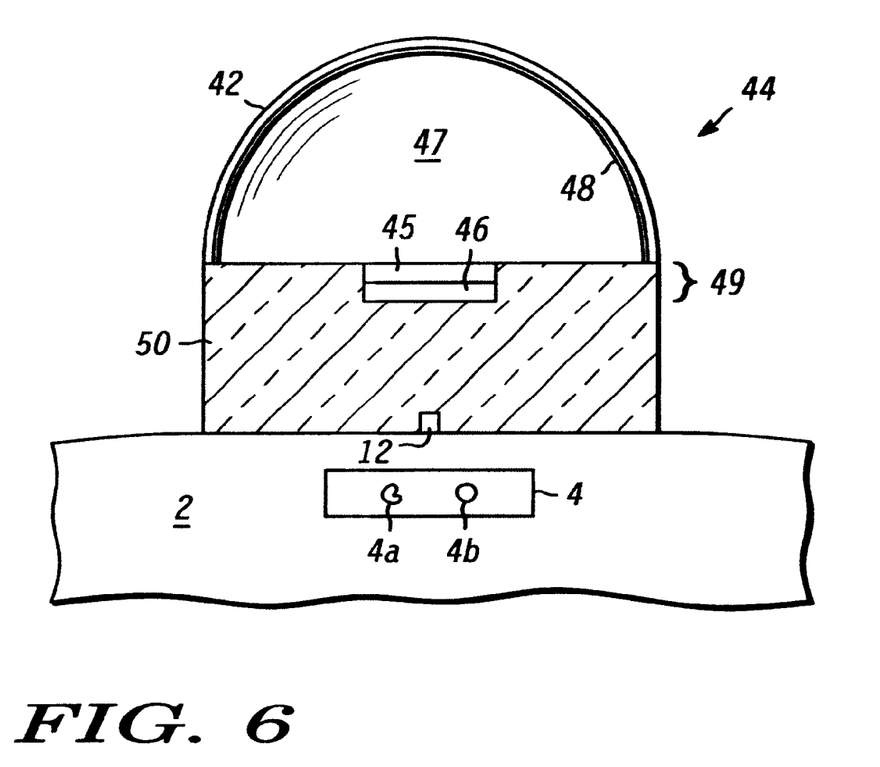
FIG. 6 illustrates a partial sectional view of a second embodiment of the portable instrument of the present invention.

In another embodiment, shown in FIG. 6, in the detection device 44, the side of a medium 50 distal to the sensor 4 may be enclosed in an enclosure 42 having a substantially hemispherical cavity 47. The medium 50 (in FIG. 6) may be formed of any material that is moldable or machineable, preferably a thin optically transparent material such as an acrylic. The material 50 may be optically transparent at at least about the wavelength range associated with the sensor 4 emissions. The medium 50 may be less than about 5 mm, preferably less than about 2 mm. The enclosure 42 may be composed of, for example, methacyrocate, polycarbonate, or PMMA, and may preferably be substantially dome shaped. The surface of the cavity 47 may be coated with a reflective material 48. The reflective material 48 is preferably Al, but may be any metal, alloy, or comparable material that is reflective at the wavelengths of interest (i.e. at least the wavelengths emitted from the sensor 4). The cavity 47 may be shaped such that radiation from the sensor 4 transmitted through the medium 50 is reflected from the reflective material 48 towards the detectors 46, thereby increasing the signal strength from the sensor 4 by allowing the receiver 49 to capture a larger amount of the emission from the sensor 4. A set of secondary filters 45 for the reflected light may preferably be disposed on the distal side of the detectors 46, which serve the same purpose as the filters 14 in the first embodiment. The enclosure 42 may be used either with or without the aperture structure, however; at least one excitation-source 12 and one detector 46 must be used.

Thus, a combination excitation-source/detection device proximate to the dermal tissue avoids the use of optical fibers, is small, lightweight, and portable. Disadvantages of using optical fibers include the necessity of aligning the fiber to impinge on the implant, guiding the emissions from the implant into the optical fiber to obtain adequate signal strength, and puncturing the dermal tissue thereby introducing an infection path to the subcutaneous tissue under the dermal tissue. The present invention, however, does not require absolute alignment of the excitation-source or detection device, merely entailing a gross enough alignment to illuminate a portion of the implant and receive a sufficient signal. Nor does the present invention involve formation of an infection path, as the dermal tissue remains unbroken.

While the invention has been described with reference to specific embodiments, the description is illustrative of the invention and not to be construed as limiting the invention. Various modifications and applications may occur to those skilled in the art without departing from the true spirit and scope of the invention as defined in the appended claims.

I claim:

1. An optical detection system comprising:
   a sensor disposed beneath a user's dermal tissue, the sensor comprising:
      a labeled analogue that emits a first electromagnetic signal of a first wavelength upon being irradiated by radiation; and
      a reference that emits a second electromagnetic signal of a second wavelength upon being irradiated by radiation; and
   a portable instrument disposed external to the user's dermal tissue and above and adjacent to the sensor, the portable instrument comprising:
      an optical excitation-source that generates radiation, the radiation penetrating the dermal tissue and irradiating the sensor;
      a receiver that detects and discriminates between the first and second electromagnetic signals and produces a first electrical signal corresponding to the first electromagnetic signal and a second electrical signal corresponding to the second electromagnetic signal; and
      logic that receives and processes the first and second electrical signals and generates from the first and second electrical signals an indication of a detected analyte level.

2. The system of claim 1, the receiver comprising:
   a first detector that detects the first electromagnetic signal and produces the first electrical signal; and
   a second detector that detects the second electromagnetic signal and produces the second electrical signal,
   wherein, of the first and second electromagnetic signals, the first detector detects only the first electromagnetic signal and the second detector detects only the second electromagnetic signal.

3. The system of claim 2, the first detector comprising a first broad band detector that detects the first and second electromagnetic signals and a first filter that filters the second electromagnetic signal, the first filter disposed such that the first and second electromagnetic signals impinge on the first filter before the first broad band detector, the second detector comprising a second broad band detector that detects the first and second electromagnetic signals and a second filter that filters the first electromagnetic signal, the second filter disposed such that the first and second electromagnetic signals impinge on the second filter before the second broad band detector.

4. The system of claim 3, further comprising an enclosure having a substantially hemispherical cavity and opposing the receiver, a reflecting film on an inner surface of the cavity, the first and second electromagnetic signals reflected by the reflecting film and impinging on the receiver.

5. The system of claim 1, further comprising an optical element disposed between the sensor and the receiver, the optical element having a first surface exposed to air, the first surface of the optical element having a first anti-reflection coating, the optical element directing the first and second electromagnetic signals that are transmitted through the optical element such that the first and second electromagnetic signals transmitted through the optical element substantially impinge on the receiver at an angle less than about 20° from normal.

6. The system of claim 5, the optical element further comprising a second surface exposed to the dermal tissue, the second surface of the optical element having a second anti-reflection coating, wherein the optical element is disposed between the sensor and the excitation-source.

7. The system of claim 1, wherein the logic determines a concentration of the analyte.

8. The system of claim 7, the first and second electrical signals consisting of a first and a second current, the logic comprising an analog-to-digital converter to convert the first and second electrical signals to corresponding digital signals and a microprocessor to manipulate the digital signals.

9. The system of claim 7, further comprising a transmitter to transmit the digital signals to external devices.

10. The system of claim 7, the portable instrument further comprising a display to display the concentration of the analyte.

11. The system of claim 1, further comprising an optically opaque medium having an aperture, the excitation-source and receiver disposed in the aperture, the aperture defining an area of irradiation of the first and second electromagnetic signals on the receiver and substantially collimating the first and second electromagnetic signals.

12. The system of claim 11, further comprising an optical element disposed in the aperture and disposed between the sensor and the receiver, the optical element having a first surface exposed to air, the first surface of the optical element having a first anti-reflection coating, the optical element directing the first and second electromagnetic signals that are transmitted through the optical element such that the first and second electromagnetic signals transmitted through the optical element substantially impinge on the receiver at an angle less than about 20° from normal.

13. The system of claim 12, the optical element further comprising a second surface exposed to the dermal tissue, the second surface of the optical element having a second anti-reflection coating, wherein the optical element is disposed between the sensor and the excitation-source.

14. The system of claim 1, the excitation-source comprising a first excitation laser to selectively excite the labeled analogue and a second excitation laser to selectively excite the reference.

15. The system of claim 1, the excitation-source comprising a semiconductor laser diode that emits energy having a wavelength of from about 400 nm to about 2 $\mu$m.

16. The system of claim 1, the excitation-source irradiating substantially an entire volume of the sensor.

17. The system of claim 1, the first electromagnetic signal having a wavelength of greater than about 630 nm, the second electromagnetic signal having a wavelength of greater than about 670 nm, the first and second electromagnetic signals having wavelengths that do not substantially overlap.

18. The system of claim 1, wherein the receiver is disposed more distal to the sensor than the excitation-source.

19. The system of claim 1, wherein the receiver has a surface opposing the sensor upon which the first and second electromagnetic signals substantially impinge on the surface at an angle less than about 20° from normal to the surface.

20. The system of claim 1, wherein the analogue is a fluorescently labeled analogue and the reference is a quantum dot or an organic dye.

21. An optical detection system comprising:
a sensor disposed beneath a user's dermal tissue, the sensor comprising:
a labeled analogue that emits a first electromagnetic signal of a first wavelength upon being irradiated by radiation; and
a reference that emits a second electromagnetic signal of a second wavelength upon being irradiated by radiation; and
a portable instrument disposed external to the user's dermal tissue and above and adjacent to the sensor, the portable instrument comprising:
an optical excitation-source that generates radiation, the radiation penetrating the dermal tissue and irradiating the sensor;
a receiver that detects and discriminates between the first and second electromagnetic signals and produces a first electrical signal corresponding to the first electromagnetic signal and a second electrical signal corresponding to the second electromagnetic signal and having a surface opposing the sensor;
an optical element that receives the first and second electromagnetic signals and directs the first and second electromagnetic signals to substantially impinge on the receiver at an angle less than about 20° from normal; and
logic that receives and processes the first and second electrical signals and generates from the first and second electrical signals an indication of a detected analyte level.

22. The system of claim 21, the receiver comprising
a first detector that detects the first electromagnetic signal and produces the first electrical signal; and
a second detector that detects the second electromagnetic signal and produces the second electrical signal,
wherein, of the first and second electromagnetic signals, the first detector detects only the first electromagnetic signal and the second detector detects only the second electromagnetic signal.

23. The system of claim 22, the first detector comprising a first broad band detector that detects the first and second electromagnetic signals and a first filter that filters the second electromagnetic signal, the first filter disposed such that the first and second electromagnetic signals impinge on the first filter before the first broad band detector, the second detector comprising a second broad band detector that detects the first and second electromagnetic signals and a second filter that filters the first electromagnetic signal, the second filter disposed such that the first and second electromagnetic signals impinge on the second filter before the second broad band detector.

24. The system of claim 21, wherein the optical element is a lens.

25. The system of claim 21, wherein the optical element is an aperture.

26. A method of determining a concentration of an analyte in an implanted optical irradiation system, the method comprising:
   implanting a sensor beneath a user's dermal tissue, the sensor comprising a labeled analogue that emits a first electromagnetic signal of a first wavelength upon being irradiated by radiation and a reference that emits a second electromagnetic signal of a second wavelength upon being irradiated by and absorbing radiation;
   providing a portable instrument comprising an excitation-source and a detector;
   positioning the portable instrument external to the user's dermal tissue and above and adjacent to the sensor;
   irradiating the labeled analogue and the reference contained in the sensor through the dermal tissue such that the radiation penetrates the user's dermal tissue and the labeled analogue absorbs energy emitted from the excitation-source and emits the first electromagnetic signal and the reference absorbs energy emitted from the excitation-source and emits the second electromagnetic signal;
   detecting the first and second electromagnetic signals impinging on the detector;
   discriminating between the first and second electromagnetic signals detected by the receiver;
   producing a first electrical signal corresponding to the first electromagnetic signal and a second electrical signal corresponding to the second electromagnetic signal; and
   generating from the first and second electrical signals an indication of a detected analyte level.

27. The method of claim 26, further comprising filtering the first and second electromagnetic signals prior to the first and second electromagnetic signals impinging on the detector.

28. The method of claim 26, further comprising directing the first and second electromagnetic signals toward the receiver such that the first and second electromagnetic signals substantially impinge on the detector at the angle less than about 20° from normal to the surface.

29. The method of claim 28, the directing being provided by an aperture.

30. The method of claim 28, the directing being provided by a lens treated with different anti-reflection coatings on opposing surfaces between the excitation-source and the sensor.

31. The method of claim 26, further comprising converting the first and second electrical signals to corresponding digital signals, and transmitting the digital signals to a microprocessor.

32. The method of claim 31, further comprising transmitting the digital signals to an external device.

33. The method of claim 26, further comprising converting the first and second electrical signals to corresponding voltages, calculating a ratio between the first and second voltages, normalizing the first voltage using the ratio, converting the normalized voltage to a digital signal, and locally determining the concentration of the analyte from the digital signal.

34. The method of claim 33, further comprising transmitting the concentration to an external device.

35. The method of claim 26, further comprising converting the first and second electrical signals to corresponding voltages, calculating a ratio between the first and second voltages, normalizing the first voltage using the ratio, converting the normalized voltage to a digital signal, transmitting the digital signal to an external device, and remotely determining the concentration of the analyte from the transmitted signal.

36. The method of claim 26, further comprising determining a concentration of analyte from a single excitation pulse of the excitation-source.

37. The method of claim 26, further comprising determining the concentration of analyte from a plurality of excitation pulses of the excitation-source.

38. The method of claim 37, the determination comprising establishing the concentration of analyte by monitoring a change of intensity of the first and second electromagnetic signals over time.

39. The method of claim 26, further comprising displaying a concentration of the analyte.

40. The method of claim 26, further comprising selecting the excitation-source to emit energy having a wavelength of greater than about 600 nm.

41. The method of claim 26, the irradiating comprising irradiating substantially an entire volume of the sensor.

42. A method of determining a concentration of an analyte in an implanted optical irradiation system, the method comprising:
   implanting a sensor beneath a user's dermal tissue, the sensor comprising a labeled analogue and a reference that emits electromagnetic signals upon being irradiated by and absorbing radiation;
   providing a portable instrument comprising an excitation-source and a detector;
   positioning the portable instrument external to the user's dermal tissue and above and adjacent to the sensor;
   irradiating the labeled analogue and the reference contained in the sensor through the dermal tissue such that the radiation penetrates the user's dermal tissue and the labeled analogue and the reference absorbs energy emitted from the excitation-source and emit the electromagnetic signals;
   directing the electromagnetic signals such that electromagnetic signals impinging on the detector substantially impinge on the detector at an angle less than about 20° from normal;
   detecting the electromagnetic signals impinging on the detector;
   producing a electrical signals corresponding to the electromagnetic signals; and
   generating from the electrical signals an indication of a detected analyte level.

43. The method of claim 42, further comprising filtering the electromagnetic signals prior to the electromagnetic signals impinging on the detector.

44. The method of claim 42, the directing being provided by an aperture.

45. The method of claim 42, the directing being provided by a lens treated with different anti-reflection coatings on opposing surfaces between the excitation-source and the sensor.

46. The method of claim 42, further comprising converting the electrical signals to corresponding digital signals, and transmitting the digital signals to a microprocessor.

47. The method of claim 46, further comprising transmitting the digital signals to an external device.

48. The method of claim 42, further comprising converting the signals to corresponding voltages, calculating a ratio between the voltages, normalizing one of the voltages using the ratio, converting the normalized voltage to a digital signal, and locally determining the concentration of the analyte from the digital signal.

49. The method of claim 48, further comprising transmitting the concentration to an external device.

50. The method of claim 42, further comprising converting the electrical signals to corresponding voltages, calculating a ratio between the voltages, normalizing one of the voltages using the ratio, converting the normalized voltages to a digital signal, transmitting the digital signal to an external device, and remotely determining the concentration of the analyte from the transmitted signal.

51. The method of claim 42, further comprising determining a concentration of analyte from a single excitation pulse of the excitation-source.

52. The method of claim 42, further comprising determining the concentration of analyte from a plurality of excitation pulses of the excitationsource.

53. The method of claim 52, the determination comprising establishing the concentration of analyte by monitoring a change of intensity of the electromagnetic signals over time.

54. The method of claim 42, further comprising displaying a concentration of the analyte.

55. The method of claim 42, further comprising selecting the excitation-source to emit energy having a wavelength of greater than about 600 nm.

56. The method of claim 42, the irradiating comprising irradiating substantially an entire volume of the sensor.

* * * * *